(12) United States Patent
Marcotulli et al.

(10) Patent No.: US 11,129,843 B2
(45) Date of Patent: Sep. 28, 2021

(54) TREATING AND PREVENTING KIDNEY DAMAGE

(71) Applicant: Elysium Health, Inc., New York, NY (US)

(72) Inventors: Eric A. Marcotulli, New York, NY (US); Daniel A. Alminana, New York, NY (US); Leonard Pershing Guarente, Newton, MA (US); Ryan Dellinger, Azusa, CA (US); Mark Morris, New York, NY (US)

(73) Assignee: Elysium Health, Inc., New York, NY (US)

( * ) Notice: Subject to any disclaimer, the term of this patent is extended or adjusted under 35 U.S.C. 154(b) by 0 days.

(21) Appl. No.: 16/607,531

(22) PCT Filed: Apr. 23, 2018

(86) PCT No.: PCT/US2018/028807
§ 371 (c)(1),
(2) Date: Oct. 23, 2019

(87) PCT Pub. No.: WO2018/200356
PCT Pub. Date: Nov. 1, 2018

(65) Prior Publication Data
US 2020/0069711 A1 Mar. 5, 2020

Related U.S. Application Data

(60) Provisional application No. 62/489,095, filed on Apr. 24, 2017.

(51) Int. Cl.
*A61K 31/706* (2006.01)
*A61K 31/09* (2006.01)
*A61P 13/12* (2006.01)

(52) U.S. Cl.
CPC ............ *A61K 31/706* (2013.01); *A61K 31/09* (2013.01); *A61P 13/12* (2018.01)

(58) Field of Classification Search
None
See application file for complete search history.

(56) References Cited

FOREIGN PATENT DOCUMENTS

| WO | WO-2015/186068 A1 | 12/2015 | |
|---|---|---|---|
| WO | WO-2016/149277 A1 | 9/2016 | |
| WO | WO-2016200447 A1 * | 12/2016 | ......... A61K 31/706 |
| WO | WO-2017/161165 A1 | 9/2017 | |
| WO | WO-2018/200356 | 11/2018 | |
| WO | WO-2019/006262 A1 | 1/2019 | |
| WO | WO-2019/126482 A1 | 6/2019 | |

OTHER PUBLICATIONS

Denker, B., Robles-Osorio, M. L., & Sabath, E. (2011). Recent advances in diagnosis and treatment of acute kidney injury in patients with cancer. European Journal of Internal Medicine, 22(4), 348-354. (Year: 2011).*
Bagavant, H., & Fu, S. M. (2009). Pathogenesis of kidney disease in systemic lupus erythematosus. Current opinion in rheumatology, 21(5), 489. (Year: 2009).*
Fernandez-Sola et al., "Adult-Onset Mitochondrial Myopathy," Postgad Med J, 68:212-215 (1992).
International Search Report and Written Opinion for International Application No. 18/28807 dated Jul. 12, 2018.
Medicalxpress, "Mitochondrial Metabolism Linked to Acute Kidney Injury," (2016).
Neyrs. "Acute Kidney Injurt (AKI)," National Kidney Foundation, (2017).
Onhealth, "What is Low Blood Pressure (Hypotension)?," (2016).
Sciencedaily, "Mitochondrial Troublemakers Unmasked in Lupus," University of Washington Health Sciences, (2016).
Dellinger et al., "Repeat dose NRPT (nicotinamide riboside and pterostilbene) increases NAD+ levels in humans safely and sustainably: a randomized, double-blind, placebo-controlled study,", NPJ Aging and Mechanisms of Disease, 3(1): 9 pages (2017).
Extended European Search Report for EP Application No. 18791750.5 dated Dec. 17, 2020.
Petra Simic et al., "Nicotinamide riboside with pterostilbene (NRPT) increases NAD+ in patients with acute kidney injury (AKI): a randomized, double-blind, placebo-controlled, stepwise safety study of escalating doses of NRPT in patients with AKI," BMC Nephrology, 21 (342): 9 pages (2020).
Petra Simic., "History of Changes for Study: NCT03176628—Pharmacokinetics, Pharmacodynamics and Safety of Basis in Acute Kidney Injury Study (BAKIS)", ClinicalTrials.gov Archive, Jun. 2, 2017: 4 pages (2017).
Xia et al., "Pterostilbene attenuates acute kidney injury in septic mice," Experimental and Therapeutic Medicine, 15(3): 3551-3555 (2018).

* cited by examiner

*Primary Examiner* — Dale R Miller
(74) *Attorney, Agent, or Firm* — Foley Hoag LLP

(57) ABSTRACT

Provided herein are methods and compositions related to treating and/or preventing kidney related diseases and disorders, treating and/or preventing acute kidney injury, and for improving kidney health in a subject by administering to the subject (e.g., orally administering to the subject) a composition comprising nicotinamide riboside and/or pterostilbene.

45 Claims, No Drawings

TREATING AND PREVENTING KIDNEY DAMAGE

RELATED APPLICATIONS

This application is a § 371 national-stage application based on PCT/US18/28807, filed Apr. 23, 2018 which claims the benefit of priority to U.S. Provisional Patent Application Ser. No. 62/489095, filed Apr. 24, 2017, each of which hereby incorporated by reference in its entirety.

BACKGROUND

Kidney failure, also known as renal failure or renal insufficiency, is a medical condition of impaired kidney function in which the kidneys fail to adequately filter metabolic wastes from the blood. Kidney damage or failure occurs in a number of acute (e.g., as a result of acute kidney injury) and chronic (e.g., as a result of kidney disease) clinical conditions. Kidney failure causes thousands or deaths each year in the United States. Accordingly, there is a great need for new compositions and methods for the treatment and prevention of kidney failure and its underlying causes.

SUMMARY

Provided herein are methods and compositions related to treating and/or preventing kidney injury, kidney related diseases or disorders, and for improving kidney health in a subject by administering to the subject (e.g., orally administering to the subject) a composition comprising a compound of Formula I or Formula II (e.g., nicotinamide riboside), and/or a compound of Formula III (e.g., pterostilbene).

In certain aspects, the methods and compositions provided herein relate to the treatment and/or prevention of kidney damage in a subject by administering to the subject (e.g., orally administering to the subject) a composition comprising a compound of Formula I or Formula II (e.g., nicotinamide riboside) and/or a compound of Formula III (e.g., pterostilbene). In certain embodiments, the kidney damage is the result of cancer, decreased blood flood to the kidneys (i.e., ischemia), back up of urine in the kidneys, sepsis, trauma, autoimmune disease, drug-induced toxicity (e.g., non-steroidal anti-inflammatory (NSAID) induced nephrotoxicity), lead poisoning, and/or severe dehydration.

In certain aspects, the methods and compositions provided herein relate to the treatment and/or prevention of acute kidney injury in a subject by administering to the subject (e.g., orally administering to the subject) a composition comprising a compound of Formula I or Formula II (e.g., nicotinamide riboside) and/or a compound of formula III (e.g., pterostilbene). In some embodiments, the acute kidney injury is the result of decreased blood flow to the kidneys (i.e., ischemic injury). Decreased blood flow to the kidneys may be a result of hypotension, blood loss, severe diarrhea, heat attack, heart failure, deceased heart function, organ failure, drug-induced nephrotoxicity (e.g., NSAID induced nephrotoxicity), allergic reactions, burns, trauma (e.g., blunt trauma), and/or surgery. In some embodiments, the acute kidney injury is the result of cancer (e.g., multiple myeloma), sepsis, vasculitis, interstitial nephritis, scleroderma, tubular necrosis, glomerulonephritis, or thrombotic microangiopathy. In some embodiments, the acute kidney injury is the result of blockage of the urinary tract. Blockage of the urinary tract may be caused by bladder cancer, prostate cancer, cervical cancer, an enlarged prostate, kidney stones, or blood clots in the urine. In certain aspects, provided herein are methods of treating kidney disease (e.g., chronic kidney disease) in a subject by administering to the subject (e.g., orally administering to the subject) a composition comprising a compound of Formula I or Formula II (e.g., nicotinamide riboside) and/or a compound of Formula III (e.g., pterostilbene). In some embodiments, the chronic kidney disease is the result of an immune system disease (e.g., lupus), long term viral disease (e.g., HIV/AIDS, hepatitis B, or hepatitis C), urinary tract infections, polycystic kidney disease, and/or inflammation of glomeruli.

In certain embodiments of the compositions and methods provided herein, the composition comprises a compound of Formula I or Formula II (e.g., nicotinamide riboside) (e.g., at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg or at least 600 mg of a compound of Formula I or Formula II (e.g., nicotinamide riboside)). In some embodiments, the composition comprises a compound of Formula III (e.g., pterostilbene) (e.g., at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg or at least 150 mg of a compound of formula III (e.g., pterostilbene)). In certain embodiments, the composition comprises both a compound of Formula I or Formula II (e.g., nicotinamide riboside) (e.g., at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg or at least 600 mg of a compound of Formula I or Formula II (e.g., nicotinamide riboside)) and a compound of Formula III (e.g., pterostilbene) (e.g., at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg or at least 150 mg of a compound of formula III (e.g., pterostilbene)).

In certain embodiments, the method comprises administering a plurality of doses of the composition. In some embodiments, at least 7 doses of the composition are administered. In some embodiments, at least 30 doses of the composition are administered. In some embodiments, at least 60 or more doses of the composition are administered. In some embodiments, each dose comprises at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg or at least 600 mg of a compound of Formula I or Formula II (e.g., nicotinamide riboside). In some embodiments, each dose comprises at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg or at least 150 mg of a compound of formula III (e.g., pterostilbene). In certain embodiments, each dose comprises at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg or at least 600 mg of a compound of Formula I or Formula II (e.g., nicotinamide riboside) at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg or at least 150 mg of a compound of formula III (e.g., pterostilbene).

In certain embodiments, a dose of the composition is administered at regular intervals over a period of time. In some embodiments, a dose of the composition is administered at least once a week. In some embodiments, a dose of the composition is administered at least twice a week. In certain embodiments, a dose of the composition is administered at least three times a week. In some embodiments, a dose of the composition is administered at least once a day. In some embodiments, a dose of the composition is administered at least twice a day. In some embodiments, doses of the composition are administered for at least 1 week, for at least 2 weeks, for at least 3 weeks, for at least 4 weeks, for at least 1 month, for at least 2 months, for at least 3 months, for at least 4 months, for at least 5 months, for at least 6 months or for at least 1 year.

In certain embodiments, the composition is formulated for oral delivery. In some embodiments, the composition is formulated as a pill, a tablet, or a capsule. In some embodiments, the composition is administered orally. In certain embodiments, the composition is self-administered.

DETAILED DESCRIPTION

General

Provided herein are methods and compositions related to treating and/or preventing kidney injury, treating and/or preventing kidney related diseases and disorders, and for improving kidney health in a subject by administering to the subject (e.g., orally administering to the subject) a composition comprising a compound of Formula I or Formula II (e.g., nicotinamide riboside) and/or a compound of Formula III (e.g., pterostilbene). In certain aspects, provided herein are methods and compositions related to treating or preventing kidney damage and/or acute kidney injury. In some aspects, provided herein are methods and compositions for increasing the blood flow to the kidneys.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering. Administration of a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

The phrase "pharmaceutically-acceptable carrier" as used herein means a pharmaceutically-acceptable material, composition or vehicle, such as a liquid or solid filler, diluent, excipient, or solvent encapsulating material.

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

As used herein, a therapeutic that "prevents" a disorder or condition refers to a compound that, when administered to a statistical sample prior to the onset of the disorder or condition, reduces the occurrence of the disorder or condition in the treated sample relative to an untreated control sample, or delays the onset or reduces the severity of one or more symptoms of the disorder or condition relative to the untreated control sample.

Compositions

Provided herein are pharmaceutical compositions comprising a compound of Formula I or Formula II (e.g., nicotinamide riboside) and/or a compound of formula III (e.g., pterostilbene).

Nicotinamide riboside is a pyridine-nucleoside form of niacin (i.e., vitamin $B_3$) that serves as a precursor to nicotinamide adenine dinucleotide ($NAD^+$). As used herein, "nicotinamide riboside" also includes nicotinamide riboside salts, such as nicotinamide riboside chloride. The chemical structure of nicotinamide riboside is provided below:

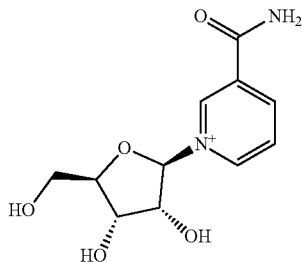 [SMILES: NC(=O)c1ccc[n+]([C@@H]2O[C@H](CO)[C@@H](O)[C@H]2O)c1]

In some embodiments, provided herein are pharmaceutical compositions comprising a compound represented by Formula (I) or a pharmaceutically acceptable salt thereof:

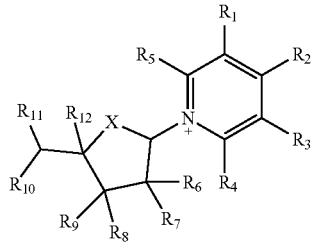

(I)

wherein, independently for each occurrence:

$R_1$, $R_2$, and $R_3$ are selected from hydrogen, halogen, —CN, —$NO_2$, —$OR_{14}$, —$N(R_{14})_m$, —$R_{13}$, substituted or unsubstituted ($C_1$-$C_6$)alkyl, cycloalkyl, heterocycloalkyl, aryl, heteroaryl, aralkyl, and heteroaralkyl;

$R_4$ and $R_5$ are selected from hydrogen, halogen, —CN, —$NO_2$, —$OR_{14}$, —$N(R_{14})_m$, substituted or unsubstituted ($C_1$-$C_6$)alkyl, cycloalkyl, heterocycloalkyl, aryl, heteroaryl, aralkyl, and heteroaralkyl;

$R_6$, $R_8$, $R_{11}$, and $R_{12}$ are selected from hydrogen, ($C_1$-$C_6$)alkyl, —(($C_1$-$C_6$)alkylene)$N(R_{14})_m$, —$C(O)(($C_1$-$C_6$)alkylene)N($R_{14}$)$_m$, cycloalkyl, heterocycloalkyl, aryl, heteroaryl, aralkyl, heteroaralkyl, —$OR_{14}$, and —$N(R_{14})_m$;

$R_7$, $R_9$, and $R_{10}$ are selected from —(($C_1$-$C_6$)alkylene)N($R_{14}$)$_m$, —$OR_{14}$, and —$N(R_{14})_m$;

$R_{13}$ is selected from —$OR_{14}$, —$N(R_{14})_m$, —$C(O)(R_{14})$, —$C(O)(OR_{14})$, —$C(O)N(R_{14})_m$, —$S(O)_2(OR_{14})$, —$S(O)OR_{14}$, and —$S(O)_2N(R_{14})_m$;

$R_{14}$ is selected from hydrogen, ($C_1$-$C_6$)alkyl, cycloalkyl, heterocycloalkyl, aryl, heteroaryl, aralkyl, and heteroaralkyl; and X is O, S, or N($R_{14}$);

m is 2 or 3;

provided that at least one of $R_1$, $R_2$, and $R_3$ is $R_{13}$.

In some embodiments, $R_1$ is $R_{13}$. In some embodiments, $R_2$ is $R_{13}$. In some embodiments, $R_3$ is $R_{13}$.

In some embodiments, $R_{13}$ is selected from —$OR_{14}$, —$C(O)(R_{14})$, —$C(O)(OR_{14})$, and —$C(O)N(R_{14})_m$. In some embodiments, $R_{13}$ is selected from —$C(O)(R_{14})$, —$C(O)(OR_{14})$, and —$C(O)N(R_{14})_m$. In some embodiments, $R_{13}$ is —$C(O)N(R_{14})_m$.

In some embodiments, $R_7$, $R_9$, and $R_{10}$ are each independently —$OR_{14}$ or —$N(R_{14})_m$. In some embodiments, $R_7$, $R_9$, and $R_{10}$ are —$OR_{14}$.

In some embodiments, the compound of formula (I) is represented by Formula (II) or a pharmaceutically acceptable salt thereof:

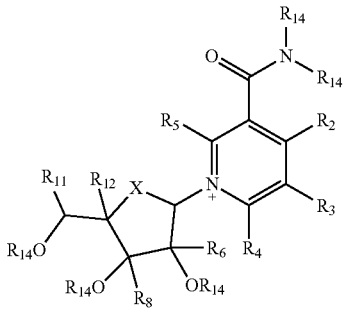

(II)

wherein, independently for each occurrence:

$R_2$ and $R_3$ are selected from hydrogen, halogen, —CN, —$NO_2$, —$OR_{14}$, —$N(R_{14})_m$, —$R_{13}$, substituted or unsubstituted ($C_1$-$C_6$)alkyl, cycloalkyl, heterocycloalkyl, aryl, heteroaryl, aralkyl, and heteroaralkyl;

$R_4$ and $R_5$ are selected from hydrogen, halogen, —CN, —$NO_2$, —$OR_{14}$, —$N(R_{14})_m$, substituted or unsubstituted ($C_1$-$C_6$)alkyl, cycloalkyl, heterocycloalkyl, aryl, heteroaryl, aralkyl, and heteroaralkyl;

$R_6$, $R_8$, $R_{11}$, and $R_{12}$ are selected from hydrogen, —$OR_{14}$, —$N(R_{14})_m$, substituted or unsubstituted ($C_1$-$C_6$)alkyl, —(($C_1$-$C_6$)alkylene)N($R_{14}$)$_m$, —$C(O)(($C_1$-$C_6$)alkylene)N($R_{14}$)$_m$, cycloalkyl, heterocycloalkyl, aryl, heteroaryl, aralkyl, and heteroaralkyl;

$R_{13}$ is selected from —$OR_{14}$, —$N(R_{14})_m$, —$C(O)(R_{14})$, —$C(O)(OR_{14})$, —$C(O)N(R_{14})_m$, —$S(O)_2(OR_{14})$, —$S(O)OR_{14}$, and —$S(O)_2N(R_{14})_m$;

$R_{14}$ is selected from hydrogen, ($C_1$-$C_6$)alkyl, cycloalkyl, heterocycloalkyl, aryl, heteroaryl, aralkyl, and heteroaralkyl; and m is 2 or 3.

In some embodiments of the compounds of formula (I) or (II), $R_1$, $R_2$, and $R_3$ are each independently, if present, selected from hydrogen, halogen, —CN, —$NO_2$, —$OR_{14}$, —$N(R_{14})_m$, —$R_{13}$, and substituted or unsubstituted ($C_1$-$C_6$) alkyl. In some embodiments, and $R_3$ are each independently, if present, selected from hydrogen, —$OR_{14}$, —$N(R_{14})_m$, and unsubstituted ($C_1$-$C_6$)alkyl. In some embodiments, $R_1$, $R_2$, and $R_3$ are each independently, if present, selected from substituted or unsubstituted ($C_1$-$C_6$)alkyl, cycloalkyl, heterocycloalkyl, aryl, heteroaryl, aralkyl, and heteroaralkyl. In some embodiments, $R_1$, $R_2$, and $R_3$ are each independently, if present, hydrogen.

In some embodiments of the compounds of formula (I) or (II), $R_4$ and $R_5$ are each independently selected from hydrogen, halogen, —CN, —$NO_2$, —$OR_{14}$, —$N(R_{14})_m$, and substituted or unsubstituted ($C_1$-$C_6$)alkyl. In some embodiments, $R_4$ and $R_5$ are each independently selected from hydrogen, —$OR_{14}$, —$N(R_{14})_m$, and unsubstituted ($C_1$-$C_6$) alkyl. In some embodiments, $R_4$ and $R_5$ are each independently selected from substituted or unsubstituted ($C_1$-$C_6$) alkyl, cycloalkyl, heterocycloalkyl, aryl, heteroaryl, aralkyl, and heteroaralkyl. In some embodiments, $R_4$ and $R_5$ are each hydrogen.

In some embodiments of the compounds of formula (I) or (II), $R_6$, $R_8$, $R_{11}$, and $R_{12}$ are selected from hydrogen, —$OR_{14}$, —$N(R_{14})_m$, unsubstituted ($C_1$-$C_6$)alkyl, —(($C_1$-$C_6$) alkylene)N($R_{14}$)$_m$, —$C(O)(($C_1$-$C_6$)alkylene)N($R_{14}$)$_m$, cycloalkyl, heterocycloalkyl, aryl, heteroaryl, aralkyl, and heteroaralkyl. In some embodiments, $R_6$, $R_8$, $R_{11}$, and $R_{12}$ are each independently selected from hydrogen, —$OR_{14}$, —$N(R_{14})_m$, unsubstituted ($C_1$-$C_6$)alkyl, —(($C_1$-$C_6$)alkylene)N(R$_{14}$)$_m$, and —C(O)((C$_1$-C$_6$)alkylene)N(R$_{14}$)$_m$. In some embodiments, R$_6$, R$_8$, R$_{11}$, and R$_{12}$ are each independently selected from hydrogen, —OR$_{14}$, and —N(R$_{14}$)$_m$. In some embodiments, R$_6$, R$_8$, R$_{11}$, and R$_{12}$ are each independently selected from unsubstituted (C$_1$-C$_6$)alkyl, cycloalkyl, heterocycloalkyl, aryl, heteroaryl, aralkyl, and heteroaralkyl. In some embodiments, R$_6$, R$_8$, R$_{11}$, and R$_{12}$ are each hydrogen.

In some embodiments, R$_7$, R$_9$, and R$_{10}$ are each independently —OR$_{14}$ or —N(R$_{14}$)$_m$. In some embodiments, R$_7$, R$_9$, and R$_{10}$ are each —OR$_{14}$. In some embodiments, R$_7$, R$_9$, and R$_{10}$ are each —OH.

In some embodiments of the compounds of formula (I) or (II), R$_{14}$ is hydrogen or (C$_1$-C$_6$)alkyl.

In some embodiments of the compounds of formula (I) or (II), X is O or N(R$_{14}$). In some embodiments, X is O.

In some embodiments of the compounds of formula (I) or (II), the compound is

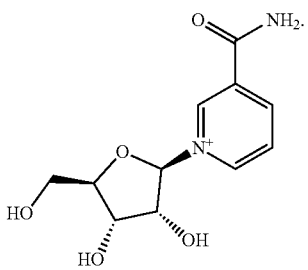

Pterostilbene is a stilbenoid and an analog of polyphenol reservatrol that has better bioavailability due to the presence of two methoxy groups that allow it to have increased lipophilic and oral absorption as well as a longer half-life due to reduced oxidation. The chemical structure of pterostilbene is provided below:

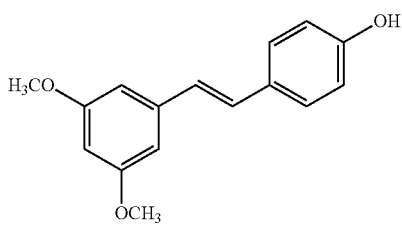 [SMILES: COc1cc(/C=C/c2ccc(O)cc2)cc(OC)c1]

In some embodiments, provided herein are pharmaceutical compositions comprising a compound represented by Formula (III) or a pharmaceutically acceptable salt thereof:

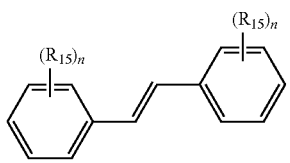

wherein, independently for each occurrence:
R$_{15}$ is selected from halogen, —CN, —NO$_2$, —OR$_{16}$, —N(R$_{16}$)$_p$, —S(O)$_2$(OR$_{16}$), —S(O)OR$_{16}$, substituted or unsubstituted (C$_1$-C$_6$)alkyl, cycloalkyl, heterocycloalkyl, aryl, heteroaryl, aralkyl, and heteroaralkyl;

R$_{16}$ is selected from hydrogen, (C$_1$-C$_6$)alkyl, cycloalkyl, heterocycloalkyl, aryl, heteroaryl, aralkyl, and heteroaralkyl;

n is an integer from 0 to 5; and
p is 2 or 3;
provided that at least one n is 1; and at least one R$_{15}$ is —OR$_{16}$;
provided that the compound of formula (III) is not

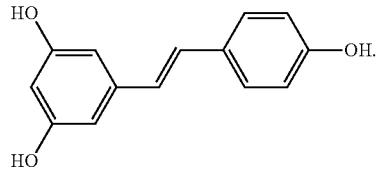

In some embodiments of the compounds of formula (III), R$_{15}$ is selected from, halogen, —CN, —NO$_2$, —OR$_{16}$, —N(R$_{16}$)$_p$, and substituted or unsubstituted (C$_1$-C$_6$)alkyl. In some embodiments, R$_{15}$ is selected from —OR$_{16}$, —N(R$_{16}$)$_p$, and unsubstituted (C$_1$-C$_6$)alkyl. In some embodiments, R$_{15}$ is selected from substituted or unsubstituted (C$_1$-C$_6$)alkyl, cycloalkyl, heterocycloalkyl, aryl, heteroaryl, aralkyl, and heteroaralkyl. In some embodiments, R$_{15}$ is —OR$_{16}$. In some embodiments, R$_{15}$ is —OR$_{16}$; and R$_{16}$ is hydrogen or (C$_1$-C$_6$)alkyl. In some embodiments, R$_{15}$ is —OR$_{16}$; and R$_{16}$ is (C$_1$-C$_6$)alkyl, cycloalkyl, heterocycloalkyl, aryl, heteroaryl, aralkyl, and heteroaralkyl. In some embodiments, R$_{15}$ is —OR$_{16}$, and R$_{16}$ is (C$_1$-C$_6$)alkyl. In some embodiments, R$_{15}$ is —OR$_{16}$ and —R$_{16}$ is (C$_1$-C$_6$) alkyl, cycloalkyl, or heterocycloalkyl.

In some embodiments, n is 1, 2, or 3. In some embodiments, n is 1 or 2.

In some embodiments, p is 2. In some embodiments, p is 3.

In one aspect, the provided herein are pharmaceutically acceptable compositions which comprise a therapeutically-effective amount of one or more of the compounds described herein (e.g., nicotinamide riboside and/or pterostilbene), formulated together with one or more pharmaceutically acceptable carriers (additives) and/or diluents. In another aspect, the agents described herein can be administered as such, or administered in mixtures with pharmaceutically acceptable carriers and can also be administered in conjunction with other agents. Conjunctive therapy thus includes sequential, simultaneous and separate, or co-administration of one or more compounds of the invention, wherein the therapeutic effects of the first administered has not entirely disappeared when the subsequent compound is administered.

As described in detail below, the pharmaceutical compositions described herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; or (3) sublingually.

In some embodiments, the composition comprises additional agents. For example, the composition may comprise a nutritional agent, such as an antioxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations of the compounds described herein may be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the agent which produces a therapeutic effect.

In certain embodiments, a formulation described herein comprises an excipient, including, but not limited to, cyclodextrins, liposomes, micelle forming agents, e.g., bile acids, and polymeric carriers, e.g., polyesters and polyanhydrides; and an agent of the invention. In some embodiments, an aforementioned formulation renders orally bioavailable an agent of the invention. Methods of preparing these formulations or compositions may include the step of bringing into association a compound of the invention with the carrier and, optionally, one or more accessory ingredients.

Liquid dosage forms for oral administration of the formulations provided herein include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations provided herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. A compound of the invention may also be administered as a bolus, electuary, or paste.

In solid dosage forms of the invention for oral administration (e.g., capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions described herein may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Pharmaceutical compositions provided herein suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Therapeutic Methods

Provided herein are methods of preventing or treating kidney damage, preventing or treating kidney injury (e.g., acute kidney injury), and/or increasing blood flow to the kidneys in a subject by administering to the subject (e.g., a subject in need thereof) a composition disclosed herein (i.e., a composition comprising a compound of Formula I or Formula II (e.g., nicotinamide riboside) and/or a compound of Formula III (e.g., pterostilbene)). The subject may have kidney damage, acute kidney injury, and/or a kidney disease.

As used herein, kidney damage may refer to a medical condition of impaired kidney function in which the kidneys fail to adequately filter metabolic wastes from the blood. In some embodiments, kidney damage is also indicative of kidney failure. Examples of conditions that may cause kidney damage include, but are not limited to decreased blood flood to the kidneys, back up of urine in the kidneys, sepsis, trauma (e.g., such as blunt trauma), an autoimmune disease, drug-induced nephrotoxicity (e.g., NSIAD induced nephrotoxicity), heavy mental poisoning (e.g., lead poisoning), or severe dehydration.

In some aspects, provided herein are methods of treating or preventing acute kidney injury (i.e., in a subject in need thereof). In some embodiments, acute kidney injury is an episode of kidney failure or kidney damage that happens within a few hours or a few days. Acute kidney injury, as used herein, may be characterized by abrupt deterioration in kidney function. In some embodiments, the subject has acute kidney injury, and the acute kidney injury may manifest by an increase in serum creatinine level with or without reduced urine output. In some embodiments, the subject has increased serum creatinine levels. In some embodiments, the subject may have reduced urine output. In some embodiments, the subject has acute kidney injury, and the acute kidney injury may be prerenal (e.g., caused by decreased renal blood flow), intrinsic renal (e.g., caused by a process within the kidneys), or postrenal (e.g., caused by inadequate drainage of urine distal to the kidneys).

Acute kidney injury or kidney damage may be a result of use (e.g., overuse) of medications, such as NSAIDs, angiotensin-converting enzyme inhibitors, angiotensin receptor blockers, cyclosporine, diuretics, tacrolimus, penicillin analogues, cephalosporins, sulfonamides, ciprofloxacin, acyclovir, rifampin, phenytoin, interferon, or proton pump inhibitors. Other causes of acute kidney injury and kidney damage include cardiorenal syndrome, hepatorenal syndrome, abdominal compartment syndrome, hypercalcemia, sepsis, neurogenic shock, infections of the renal parenchyma, glomerulonephritis, viral infections (such as Epstein-Barr virus infections or cytomegalovirus infections), bacterial infections (e.g., bacterial infections caused by bacteria of the *Streptococcus* or *Legionella* species), or fungal infections (e.g., fungal infections caused by candidiasis or histoplasmosis). In some embodiments, the acute renal injury and/or kidney damage is caused by a systemic disease, such as sarcoidosis or lupus.

Additional examples of conditions that cause acute kidney injury and kidney damage include cancer (e.g., multiple myeloma), prolonged hypotension, renal vein thrombosis, malignant hypertension, scleroderma renal crisis, renal atheroembolic disease, renal infarction vasculitis, interstitial nephritis, scleroderma, and or conditions that cause inflammation of or damage to the kidney tubules, such as tubular necrosis, glomerulonephritis, or thrombotic microangiopathy.

In some embodiments, the acute kidney injury and/or kidney damage is caused by a decrease in blood flow to the kidney. Conditions that may cause a decrease in blood flow to the kidneys includes, for example, blood loss, severe diarrhea, heat attack, heart failure, deceased heart function, organ failure, allergic reactions, burns, and/or trauma. In some embodiments, the subject has undergone surgery, and the subject's blood vessels have been clamped, leading to a decrease of blood flow to the kidneys. In some embodiments, the acute kidney injury or kidney damage is the result of a blockage of the urinary tract. A blockage of the urinary tract may be the result of, for example, neurogenic bladder, retroperitoneal fibrosis, bladder cancer, prostate cancer, cervical cancer, an enlarged prostate, kidney stones, blood clots, or tumors.

In some embodiments, the subject has a kidney disease. A kidney disease is any condition that affects the kidney's ability to filter compounds out of blood, filter extra water out of blood, and/or help control blood pressure. Kidney disease may be caused by diabetes, hypertension, a systemic disease (e.g., lupus), viral disease (e.g., HIV/AIDS, hepatitis B, or hepatitis C), urinary tract infections, a genetic disease, such as polycystic kidney disease, or any condition that results in the inflammation of kidney glomeruli.

In some embodiments, the subject's kidney function may be measured prior, during or after administration of a composition disclosed herein. Kidney function may be evaluated as a function of glomerular filtration rate, urine output, or the level of other biomedical markers of kidney health, such as creatinine, urea, nitrogen, phosphorus, or potassium. Markers such as creatinine, urea, nitrogen, phosphorus, or potassium may be measured in the urine or through a blood test.

Actual dosage levels and administration regimen of the compositions disclosed herein may be varied so as to obtain an amount of a compound of Formula I or Formula II (e.g., nicotinamide riboside) and/or a compound of formula III (e.g., pterostilbene) that is effective to achieve the desired therapeutic response for a particular patient, composition, and mode of administration, without being toxic to the patient.

In some embodiments, administration of the composition comprises administration of the composition in one or more dose(s). In some embodiments, administration of the composition comprises administration of the composition in one or more, five or more, ten or more, twenty or more, thirty or more, forty or more, fifty or more, one hundred or more, or one thousand or more dose(s). In some embodiments, the dose comprises at least 25 mg, at least 50 mg, at least 75 mg, at least 100 mg, at least 125 mg, at least 150 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 550 mg, at least 600 mg, at least 650 mg, at least 700 mg, at least 750 mg, at least 800 mg, or at least 850 mg of a compound of Formula I or Formula II (e.g., nicotinamide riboside). In some embodiments, the dose comprises at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 90 mg, at least 95 mg, at least 100 mg, at least 110 mg, at least 120 mg, at least 130 mg, at least 140 mg, at least 150 mg, at least 160 mg, least 170 mg, at least 180 mg, at least 190 mg, at least 200 mg, or at least 250 mg of a compound of formula III (e.g., pterostilbene).

The compositions disclosed herein may be administered over any period of time effective to achieve the desired therapeutic response for a particular patient, composition, and mode of administration, without being toxic to the patient. The period of time may be at least 1 day, at least 10 days, at least 20 days, at least 30, days, at least 60 days, at least three months, at least six months, at least a year, at least three years, at least five years, or at least ten years. The dose may be administered when needed, sporadically, or at regular intervals. For example, the dose may be administered monthly, weekly, biweekly, triweekly, once a day, or twice a day.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating or preventing kidney damage in a subject in need thereof comprising administering to the subject a composition comprising nicotinamide riboside and pterostilbene, wherein the administration of the composition comprises administering one or more doses of the composition, and each dose of the composition comprises at least 50 mg of pterostilbene.

2. The method of claim 1, wherein the kidney damage is the result of decreased blood flood to the kidneys, back up of urine in the kidneys, sepsis, trauma, an autoimmune disease, cancer, drug-induced nephrotoxicity, or severe dehydration.

3. The method of claim 1 or 2, wherein the kidney damage is caused by acute kidney injury.

4. A method of treating or preventing acute kidney injury comprising administering to a subject in need thereof a composition comprising nicotinamide riboside and pterostilbene, wherein the administration of the composition comprises administering one or more doses of the composition, and each dose of the composition comprises at least 50 mg of pterostilbene.

5. The method of claim 4, wherein the acute kidney injury is a result of decreased blood flow to the kidneys.

6. The method of claim 5, wherein the decreased blood flow is the result of hypotension, blood loss, severe diarrhea, heat attack, heart failure, decreased heart function, organ failure, drug-induced nephrotoxicity, trauma, or surgery.

7. The method of claim 6, wherein the drug-induced nephrotoxicity is NSAID- induced nephrotoxicity.

8. The method of claim 4, wherein the acute kidney injury is a result of cancer, sepsis, vasculitis, interstitial nephritis, scleroderma, tubular necrosis, glomerulonephritis, or thrombotic microangiopathy.

9. The method of claim 8, wherein the cancer is multiple myeloma.

10. The method of claim 4, wherein the acute kidney injury is the result of blockage of the urinary tract.

11. The method of claim 8, wherein the blockage is caused by neurogenic bladder, retroperitoneal fibrosis, bladder cancer, prostate cancer, cervical cancer, an enlarged prostate, kidney stones, blood clots, or tumors.

12. A method of treating kidney disease in a subject in need thereof comprising administering to the subject a composition comprising nicotinamide riboside and pterostilbene, wherein the administration of the composition comprises administering one or more doses of the composition, and each dose of the composition comprises at least 50 mg of pterostilbene.

13. The method of claim 12, wherein the kidney disease is the result of diabetes or hypertension.

14. The method of claim 12, wherein the kidney disease is the result of a systemic disease, a viral disease, urinary tract infections, polycystic kidney disease, or a condition resulting in inflammation of glomeruli.

15. The method of claim 14, wherein the systemic disease is lupus.

16. A method of increasing blood flow to the kidneys in a subject in need thereof comprising administering to the subject a composition comprising nicotinamide riboside and pterostilbene, wherein the administration of the composition comprises administering one or more doses of the composition, and each dose of the composition comprises at least 50 mg of pterostilbene.

17. The method of claim 16, wherein the subject has acute kidney injury, kidney damage, or kidney disease.

18. The method of claim 16, wherein each dose of the composition comprises at least 200 mg of nicotinamide riboside.

19. The method of claim 16, wherein each dose of the composition comprises at least 250 mg of nicotinamide riboside.

20. The method of claim 16, wherein each dose of the composition comprises at least 300 mg of nicotinamide riboside.

21. The method of claim 16, wherein each dose of the composition comprises at least 350 mg of nicotinamide riboside.

22. The method of claim 16, wherein each dose of the composition comprises at least 400 mg of nicotinamide riboside.

23. The method of claim 16, wherein each dose of the composition comprises at least 450 mg of nicotinamide riboside.

24. The method of claim 16, wherein each dose of the composition comprises at least 500 mg of nicotinamide riboside.

25. The method of claim 16, wherein each dose of the composition comprises at least 550 mg of nicotinamide riboside.

26. The method of claim 16, wherein each dose of the composition comprises at least 75 mg of pterostilbene.

27. The method of claim 16, wherein each dose of the composition comprises at least 100 mg of pterostilbene.

28. The method of claim 16, wherein each dose of the composition comprises at least 125 mg of pterostilbene.

29. The method of claim 16, wherein each dose of the composition comprises at least 150 mg of pterostilbene.

30. The method of claim 16, wherein two or more doses of the composition are administered.

31. The method of claim 16, wherein thirty or more doses of the composition are administered.

32. The method of claim 16, wherein fifty or more doses of the composition are administered.

33. The method of claim 16, wherein one hundred or more doses of the composition are administered.

34. The method of claim 16, wherein the dose of the composition is administered at least once a week.

35. The method of claim 16, wherein the dose is administered at least twice a week.

36. The method of claim 16, wherein the dose is administered at least three times a week.

37. The method of claim 16, wherein the dose is administered at least once a day.

38. The method of claim 16, wherein the dose is administered at least twice a day.

39. The method of claim 34, wherein the doses are administered for at least 7 days.

40. The method of claim 34, wherein the doses are administered for at least 30 days.

41. The method of claim 34, wherein the doses are administered for at least 60 days.

42. The method of claim 34, wherein the doses are administered for at least 90 days.

43. The method of claim 1, wherein the composition is formulated as a pill, a tablet, or a capsule.

44. The method of claim 1, wherein the composition is administered orally.

45. The method of claim 1, wherein the composition is self-administered.

* * * * *